United States Patent [19]

Muirhead et al.

[11] 4,206,201

[45] Jun. 3, 1980

[54] METHOD FOR PREPARING A COMPOUND CALLED ARL PER SE AND ITS USE AS MEDICINAL

[76] Inventors: Ernest E. Muirhead, 698 Valleybrook Dr., Memphis, Tenn. 38117; Byron E. Leach, 1550 N. Parkway, Memphis, Tenn. 38112; Lawrence W. Byers, 3138 Dumbarton Dr., Memphis, Tenn. 38128

[21] Appl. No.: 931,859

[22] Filed: Aug. 7, 1978

Related U.S. Application Data

[63] Continuation of Ser. No. 811,891, Jun. 30, 1977, abandoned.

[51] Int. Cl.$^2$ ............................................... A61K 35/12
[52] U.S. Cl. ..................................................... 424/103
[58] Field of Search .......................................... 424/103

[56] References Cited

U.S. PATENT DOCUMENTS

| 3,282,788 | 11/1966 | Daniels et al. | 424/103 |
| 3,683,070 | 8/1972 | Thuillier | 424/103 |

OTHER PUBLICATIONS

Muirhead et al., Chem. Abst., vol. 68 (1968), p. 37970w.
Muirhead et al., Chem Abst., vol. 76 (1972), p. 81365s.

*Primary Examiner*—Sam Rosen
*Attorney, Agent, or Firm*—Donald Brown

[57] ABSTRACT

Compound (hereinafter identified as ARL) useful as a vasodilator and antihypertensive agent. The compound is obtainable using rabbit kidney medulla by first incubating same, second, operating on the incubated material and then purifying the operated upon material to remove cholesterol, triglycerides, and etc. to leave an ARL compound.

2 Claims, No Drawings

METHOD FOR PREPARING A COMPOUND CALLED ARL PER SE AND ITS USE AS MEDICINAL

The invention described herein was made in the course of work under a grant or award from the United States Department of Health, Education and Welfare.

PRIOR APPLICATION

This application is a continuation of Ser. No. 811,891 filed June 30, 1977, now abandoned.

BRIEF BACKGROUND OF THE INVENTION

This invention is directed to ARL, a compound which exhibits acute vasodilator as well as antihypertensive properties. In the prior art, compositions were extracted from rabbit medulla and have been shown at high doses to provide antihypertensive activity and vasodepression activity (see Muirhead, E. E. et al, J. Lab. & Clin. Med. 56:167, 1960 and the other Muirhead et al references in Proceedings of the Seminar on Hypertension, Supplement to Annals of Academy of Medicine, The Academy of Singapore, V. 5, No. 3, July 1976, pp 36-44.

However, such prior compounds have been low in potency and in many cases the results were not reproducible, i.e., activity seemed to disappear on a batch by batch basis.

In the present invention it has now been possible consistently to reproduce antihypertensive activity and for the first time produce acute vasodilator activity, i.e., a reduction in blood pressure of 30-50% in less than one minute with extremely small doses, e.g., with a single dose of 5 to $20 \times 10^{-6}$ grams per kg (I.V.) of the isolated ARL compound as produced herein when administered to a rat. In addition, with this invention lowering of blood pressure is accomplished for periods of from 2 to 4 days in duration with four doses of $10-25 \times 10^{-6}$ grams of the ARL compound administered (I.V.) to the rat for two successive days.

Thus, the ARL compound of this invention is useful in mammals as vasodilators in conditions where afterload on the heart should be decreased (as an after load reducer), especially heart failure due to intrinsic disease of the heart muscle, e.g., cardiomyopathy, without producing substantial tachycardia (a side effect encountered with many acute vasodilators) or other dysfunction of the heart. The ARL compound of this invention would also be useful in treating cardiogenic shock, mitral regurgitation, acute myocardial infarction and protracted congestive heart failure at the doses above.

The ARL compound of this invention is also useful in mammals to treat high blood pressure (hypertension) by lowering arterial pressure. The ARL compound of the invention when used as antihypertensives would be administered a few times a day initially and then reduced maintenance doses would be administered to the mammal.

The normal dose of ARL compound for the treatment of mammals such as rats, dogs, cats, humans of the aforementioned conditions would be 5 to 30 micrograms/kg body weight with a single dose of about 15-20 micrograms being given to achieve acute vasodilatation or treat cardiogenic shock. For use of the compound as an antihypertensive a dosage preferably of 30 to 50 micrograms/kg would be given twice daily for two days and thereafter, a maintenance dose of 20 micrograms/kg of body weight would be administered daily. Thus, a unit dose of the ARL compound in humans would be 2 mg to 5 mg.

The ARL compound is preferably administered parenterally or less preferably, as a suppository in a pharmaceutically acceptable carrier. Most preferably, the ARL compound is injected in a suitable pharmaceutically acceptable vehicle in solution into a vein (I.V.); however, it may be injected into an artery, into muscle, i.e., intramuscularly, or subcutaneously, or may be infused I.V. in saline or Ringer's solution. The administration of ARL compound of this invention will, of course, be administered in accordance with the physician's instructions and the actual dose used will be based on the observations and discretion of the physician. The mode of administration of the ARL compound will be selected by the physician in attendance; however, best results to date have been with the parenteral I.V. injections using a single dose bolus or a multi-dose vial from which single doses of the ARL compound in solution in a pharmaceutically acceptable carrier are withdrawn. The compositions for injection must, of course, be sterile and desirably isotonic with the blood of the mammal into which they are being administered.

A suitable diluent is 2% saline and, in addition, solubilizing additives such as albumin or lecithin may be added. Advantageously, the ARL compound is suspended dissolved in a sterile diluent under aseptic conditions. Sterilization of the injection compositions may be effected by conventional techniques. In addition, injectable preparations may be made by adding sterile water to a tube containing the compound as a solid to form a unit dose or a multi-dose.

The ARL compound of this invention may be prepared from isolated rabbit medulla as follows: The rabbit medulla is removed from a slaughtered rabbit, is homogenized and incubated, e.g., from 10 minutes to 2 hrs. at about 25° to 40° C. and most preferably 37° C., approximately the body temperature of the rabbit, for a time sufficient to permit the medulla to produce a substance which, after lipid extraction, produces a yellow oil. Thereafter, the yellow oil is reduced, acetylated, passed through a silicic acid column and then purified through twice using thin layer chromatography to provide the ARL compound.

It has been found that without the incubation step amounts of material obtained from the medulla are not sufficient or cannot be detected to produce the desired end product, i.e., the ARL compound since the material which is needed to produce the ARL compound appears not to be available if conditions are not acceptable within the medulla after the medulla is removed from the body and not held under proper temperature and conditions for a sufficient time after removal from the body of the animal (rabbit).

EXAMPLE 1

A very active preparation of ARL was obtained from rabbit renal medulla according to the following seven step procedure:

Step I Incubation

New Zealand White rabbits were fasted for 40-44 hours with water ad libitum. They were then stunned by a blow on the head and decapitated. The kidneys were removed and placed in wet ice within 10-15 minutes of sacrifice, and the medullas were dissected out as rapidly as possible. To 125 g. of fresh medullas (from approximately 104 kidneys) in a one liter glass Waring Blendor cup were added 0.268 M Sorensen's phosphate buffer, pH 7.5 (125 ml), and the mixture was blended for 15 seconds at low speed and then for 2 minutes at high speed. The resulting homogenate was transferred to a 1200 ml Virtis flask and washed into the flask with sterile saline (125 ml). The homogenate was incubated for 32 minutes in a 37° C. water bath with frequent swirling. The incubated homogenate was then frozen and freeze-dried.

Step II Lipid Extraction

The lyophilized tissue powder was extracted by the Bligh and Dyer Method [*Can. J. Biochem. and Physiol.*, 37, 911 (1959)] as follows:

Water was added to give a mixture containing 80% water. Then chloroform and methanol were added to give a final solvent ratio of chloroform:methanol:water equal to 1:2:0.8. The mixture was then blended at fast speed for two minutes. Further additions of chloroform and of water, with 30 seconds of blending after each addition, gave a final solvent ratio of chloroform:methanol:water equal to 2:2:1.8. Centrifugation in a Sorvall RC 2B centrifuge (40 minutes at 5000 rpm) separated an aqueous layer (discarded) and a chloroform layer, which was drawn off and saved. The solids at the water:chloroform interface were resuspended in chloroform (1.5 volumes), blended for 30 seconds at low speed, and the mixture centrifuged 40 minutes at 5000 rpm. The chloroform layer was pooled with the above saved chloroform layer. The combined chloroform solution was evaporated under reduced pressure. Chloroform was added to the residue and evaporated under reduced pressure to remove traces of water, leaving a yellow oil (6.5 g).

Step III Vitride Reduction

The residual yellow oil from Step II was dissolved in 54.1 ml of a mixture of ethyl ether:benzene (80:20). The glass stoppered flask containing the yellow solution was swirled in cool running tap water as 10.58 ml of Vitride were added. (Vitride is a 70% solution of sodium bis (2-methoxy-ethoxy) aluminum hydride in benzene). The volume used represents 7.40 gms of the latter. A vigorous reaction ensued during the early part of the addition, but the cooling water kept it under control. The glass stopper was taped in and the flask was incubated, with occasional swirling, at 37° C. for 32 min. The flask was opened and the addition of a few drops of 4% acetic acid caused a vigorous reaction, indicating that an excess of reagent was present. Addition of a total of 129.2 ml of 4% acetic acid, cooling the flask under tap water, caused the appearance of a white gelatinous precipitate.

This suspension was extracted four times in a separatory funnel with 100 ml of ethyl ether each time. The emulsion was centrifuged 15 minutes, 2100 rpm, at 5° C. and the ether layer drawn off each time, pooled, and taken to dryness under reduced pressure. The aqueous layer above was re-extracted two times with 100 ml chloroform, and the chloroform layers obtained after centrifugation were pooled and taken to dryness under reduced pressure in the flask containing the ether extract. A final 100 ml of chloroform were added and distilled off to ensure removal of the last of the water. There resulted 5.4 gm of clear second yellow oil.

Step IV Acetylation

The 5.4 gm of clear yellow oil above were dissolved in 6.6 ml of pyridine (redistilled A R grade stored over KOH pellets). Addition of 26.2 ml of A R grade acetic anhydride caused some turbidity. Incubation at 65° C. for 32 min., with occasional swirling, followed.

This was followed by removal of pyridine and excess acetic anhydride by distillation under reduced pressure at 40° C. A final heating to 65° C. with nitrogen blowing into the flask for a short time removed practically all of the acetic anhydride. The acetylated fatty alcohols resulting, a cloudy yellow oil, weighed 5.8 grams.

Step V Column Chromatography

A 1×30 cm column was packed with silicic acid (9.0 g, Unisil ®, 100–200 mesh, acid washed, obtained from Clarkson Chemical Company, Inc., Williamsport, Pa.) suspended in chloroform. The cloudy yellow oil from Step IV was dissolved in 40 ml of the bottom phase from the solvent mixture chloroform:methanol containing 2% acetic acid:water (1:1:1), which bottom phase had been clarified by centrifugation. The solution of the cloudy yellow oil was also clarified by centrifugation and then placed on the column. The flow rate was adjusted to 3 drops every 5–7 seconds. When the solution had entered the column, a wash (50ml) of the clarified bottom phase was added; and 5 minute fractions were collected. The ARL compound was eluted with chloroform:methanol:acetic acid: water (50:25:84) with the flow rate maintained at 3 drops every 5–7 seconds and 5 minute fractions collected. Using this system the active ARL compound generally first appears in fractions 15–20 and is detected by assay. The volume of each fraction was 4–5 ml and a 20 µl aliquot was taken from each for assay.

The assay was performed by evaporating the aliquot solvent to dryness under a nitrogen stream, suspending with sonication the residue in 0.3 ml of saline containing 1 µg/ml lecithin, injecting the suspension intravenously into a one-kidney Goldblatt hypertensive rat, and monitoring the change in blood pressure in the rat.

The active fractions were combined and evaporated to dryness under a nitrogen stream in a 50° C. water bath to give a third yellow oil (14.3 mg).

Step VI Thin Layer Chromatography TLC 1

TLC plates were prepared using double strength window pane glass (5×20 and 20×20 cm) and silica gel MN-Kieselgel G-HR (Brinkmann Instrument, Inc., Cantiagne Rd., Westbury, N.Y.). The plates were layered with the silica gel 0.25 mm thick, allowed to stand at room temperature 30–45 min., and activated at 110° C. for one hour. They were stored prior to use in a cabinet containing a dessicant.

Each plate was marked 2.5 cm from the bottom edge and 10 cm above the first mark. The third yellow oil from Step V was dissolved in 450 µl of chloroform. The solution was then spotted (8 µl) onto one guide plate (5×20 cm) and the rest streaked evenly across three 20×20 cm plates. The TLC plates were developed in a paper-lined chromatography jar containing chloroform:methanol:acetic acid:water (50:25:8:3) about 1–2 cm deep until the solvent front reached the 10 cm mark. They were then removed and air dried. The guide plate was sprayed with concentrated sulfuric acid and heated to char. Based on the charred pattern obtained with the guide plate, the 20×20 cm plates were cut into four fractions: no. 1, from 0.5 cm before to 0.5 cm beyond the origin; no. 2, from 0.5 cm to 1.7 cm beyond the origin; no. 3, from 1.7 cm to 3.0 cm beyond the origin; and no. 4, from 3.0 cm to 10.0 cm beyond the origin. Each fraction was scraped into a 50 ml centrifugation tube and eluted as follows: water (7 ml ) was added to each tube and mixed thoroughly; methanol containing 2% acetic acid (14 ml) was added and shaken; chloroform (14 ml) was added and shaken for 5 minutes; and finally, water (7 ml) was added and shaken for 5 minutes. The tubes were centrifuged at 2000 rpm for about 10 minutes at 20° C. to separate the phases. The chloroform layers were removed and evaporated to dryness under a nitrogen stream. Each fraction was redissolved in chloroform (2.0 ml) and assayed as above. The antihypertensive activity was found to be concentrated in the no. 2 fraction, a fourth yellow oil (0.7 mg).

Step VII TLC 2

The fourth yellow oil from Step VI was subjected to thin layer chromatography according to the procedure of Step VI except one guide plate (5×20 cm) and one 20×20 cm plate were used and the developing solution was chloroform:methanol:concentrated aqueous ammonia (75:25:4). The activity was concentrated in a band from 0.5 to 1.6 cm beyond the origin, and the final yield of a light yellow oil ARL in 0.18 mg.

EXAMPLE 2 Infusion of ARL

A 0.2% solution of rat albumin (rat albumin, fraction V, Sigma #A-4760) in saline (0.9% saline, Cutter Laboratories) was sterilized by filtration through a 0.45 micron filter (Nolge #245-0045) and stored in a sterile multiple use vial at 0°-4° C. Immediately prior to administration, the albumin solution (1.0 ml) was added to a 12×75 mm tube containing 100 µg of the light yellow oil ARL of Example 1. Suspension of the ARL was effected by swirling the tube in an ultrasonic bath for 30 seconds. The resulting suspension was infused into a Goldblatt one-kidney hypertensive rat weighing 300 g over an 8 hr. period, i.e., at a rate of 0.125 ml./hr for the suspension (12.5 µg/hr of the light yellow oil ARL preparation). A decrease in the blood pressure was measured.

EXAMPLE 3 Bolus Administration

A suspension (0.075 ml) of light yellow oil ARL in saline prepared according to Example 2 was administered to a Goldblatt one-kidney hypertensive rat weighing 300 g by intravenous injection. An immediate, sharp drop in blood pressure of about 60% occurred within less than one minute after administration.

EXAMPLE 4 Effect of Continuous Administration Of ARL to Hypertensive Rats

The test animals were Goldblatt hypertensive rats. Each animal had a stable blood pressure in the range of 160–200 mm Hg approximately one month post preparation. Approximately one to two weeks prior to test the animals were prepared with chronic indwelling catheters for injecting intravenously and for measuring mean arterial blood pressure. Five animals were used for the treated group and five were used for the controls. The vehicle was 0.2% rat albumin dissolved in saline. A 100 µg dose of ARL (two dimensional thin layer chromatography material) was solubilized in 1.0 ml of the vehicle and given intravenously by continuous infusion to each treated rat for 8 hours (125 µl/hr). The controls were given vehicle only. The mean arterial blood pressure was monitored before and for 5 min. every 30 minutes during the 8 hour test period. The blood pressure of the treated animals decreased to near 100 mm Hg and remained at that level during the continuous infusion. The control animals remained at their pre-level during this time period. The animals were then returned to their home cages overnight and the next day their blood pressure was measured prior to giving the second continuous infusion for 8 hours. The treated group had a lower blood pressure at 24 hr. post start of the infusion and also at 48 hrs. past. The blood pressures were usually depressed 30–50 mm Hg over the pre-pressures at the 48 hr reading.

EXAMPLE 5 Effect of Injecting ARL as a Bolus

The experimental animals were Goldblatt hypertensive rats prepared as given in above example. The vehicle for this experiment was either 0.2% rat albumin or 1 mg/ml lecithin in saline. A 50 µg dose of ARL (two dimensional thin layer chromatographed material) was solubilized in 0.3 ml of the vehicle by sonication. Then after measuring the pre-mean arterial pressure, the five experimental rats were injected intravenously as a bolus small amounts until the 0.3 ml was given, being careful to maintain the blood pressure above 50 mm Hg. The five control animals were injected with the vehicle only. This same dose was administered again about 4 hours after the first dose. The rats were then returned to their home cages. The next day the above dosing of the animals was repeated. The mean arterial pressure taken at 24 hours, just prior to the third, and again at 48 hrs past first dose were generally 30–50 mm Hg below the pre-pressures while the controls remained unchanged.

EXAMPLE 6

In each of the following experiments, vehicle for ARL (made as per Example 1) was L-α-Lecithin (Dipalmitoyl) 1 mg/ml, Grand Island Biological Co., U.S.A. The ARL (the product of Example 1) was first dissolved in chloroform to facilitate removal of known amounts and after evaporating the solvent with a stream of nitrogen ARL was redissolved in Lecithin using an ultrasonic vibrator.

Direction of responses indicated by arrows.
All values are approximate to mean.
↑ -increase, ↓ -decrease, 0-no change.
1. Rats
(a) Unanesthetized Genetic Hypertensive
Method Sex: male; weight: 320–340 g; strain: New Zealand.

Pulsatile blood pressure measured directly by indwelling caudal artery catheter. Integrated heart rate recorded using tachometer triggered by arterial pressure waves. Drug injection via cannulated left jugular vein or oral.

Result i) Intravenous injection (in 0.1–0.2 ml), n = 4.
Mean initial systolic blood pressure (±S.E.M.)  171 ± 4 mm Hg.
Mean initial diastolic blood pressure (±S.E.M.) 118 ± 6 mm Hg.
Mean initial heart rate (±S.E.M.)               429 ± beats/min.

| | Mean fall in BP (±S.E.M.) | | Mean duration of hypo- | Mean (±SEM) |
|---|---|---|---|---|
| ARL µg/kg i.v. | Systolic (mm Hg) | Diastolic | tension (min) (±S.E.M.) | tachycardia (beats/min) |

-continued

| | | | | |
|---|---|---|---|---|
| 0.4 | 48 ± 2 | 35 ± 5 | 0.8 ± 0.5 | 3 ± 3 |
| 0.8 | 85 ± 6 | 49 ± 6 | 2.2 ± 0.2 | 3 ± 3 |
| 1.5 | 113 ± 5 | 68 ± 7 | 4.7 ± 1.2 | 0 |
| 3.0 | 117 ± 7 | 68 ± 2 | 7.9 ± 0.7 | 4 ± 4 |
| 6.0 | 119 ± 12 | 74 ± 6 | 12.8 ± 0.9 | 9 ± 5 |
| Vehicle (0.4 ml) | 0 | 0 | 0 | 0 |
| 12 μg/kg i.v. | 106 ± 16 | 68 ± 5 | 13.0 ± 1.1 | 3 ± 3 | ii) Intravenous infusion, n = 2.
Mean initial blood pressure (Systolic/diastolic 23/123 mm Hg).
Mean initial heart rate 414 beats/min.

| ARL μg/kg/min | Fall in systolic BP (mmHg) | Fall in diastolic BP (mmHg) | Change in Heart rate (beats/min) |
|---|---|---|---|
| 0.12 | 8 | 5 | 0 |
| 0.3 | 38 | 20 | 0 |
| 0.6 | 38 | 30 | 0 |
| 1.2 | 55 | 38 | 0 |

Hypotension sustained during infusion.

Conclusions

Hypotension followed intravenous administration, the effect involving both systolic and diastolic blood pressure. At the same time the heart rate was not importantly altered by ARL.

(b) Anesthetized
(i) Normotensive. N=2.
Method

Sex: male; mean weight: 300 g; strain: New Zealand Otago Wistar.

Anesthetic: initially chloroform, then maintained by intravenous chloralose 70 mg/kg.

ARL injected into left femoral vein (i.v.).

Blood pressure measured directly from left femoral artery.

Heart rate recorded using tachometer triggered by arterial pressure waves.

Result

| Drug i.v. (μg/kg) | Change in Systolic BP mm Hg | Change in Diastolic BP mm Hg | Duration of hypotension (min) | Change in Heart rate (beats/min) |
|---|---|---|---|---|
| Vehicle (0.4 ml) | 0 | 0 | 0 | 0 |
| ARL | | | | |
| 0.38 | ↓ 50 | ↓ 35 | 1.5 | ↑ 18 |
| 0.75 | ↓ 75 | ↓ 47 | 1.5 | ↑ 30 |
| 1.5 | ↓ 60 | ↓ 55 | 4.0 | ↑ 24 |
| 3.0 | ↓ 78 | ↓ 60 | 7.5 | ↑ 24 |
| 6.0 | ↓ 95 | ↓ 55 | 21.0 | ↑ 36 |
| 12.0 | ↓ 113 | ↓ 66 | 24.0 | ↑ 30 then ↓ 36 |

(ii) Genetic hypertensive N=2.
Method

Sex: male, mean weight approx. 300 g; strain: New Zealand.

Anesthetic: initially chloroform subsequent maintenance with intravenous chloralose 60–70 mg/kg.

ARL injected into left femoral vein.

Blood pressure recorded directly from left femoral artery.

Heart rate recorded using tachometer triggered by arterial pressure waves.

| Drug i.v. (μg/kg) | Change in Systolic BP mm Hg | Change in Diastolic BP mm Hg | Duration of hypotension (min) | Change in Heart rate (beats/min) |
|---|---|---|---|---|
| Vehicle | 0 | 0 | 0 | 0 |
| ARL | | | | |
| 0.38 | ↓ 68 | ↓ 55 | 3.0 | 0 |
| 0.75 | ↓ 75 | ↓ 60 | 6.3 | ↓ 24 |
| 1.5 | ↓ 120 | ↓ 80 | 8.6 | ↑ 30 |
| 3.0 | ↓ 160 | ↓ 100 | 13.8 | ↓ 48 |
| 6.0 | ↓ 195 | ↓ 120 | 22.3 | ↓ 48 |
| 12.0 | ↓ 205 | ↓ 125 | >42.0 | ↓ 78 |

Conclusion

Hypotension occurred in normotensive and hypertensive anesthetized rats after intravenous injections of ARL. Responses of the heart rates were variable; bradycardia being the usual effect in hypertensives whereas normotensives responded with tachycardia.

(c) Pithed. n=3.
Method

Sex: male; weight: 250–300 g; strain: New Zealand Otago Wistar.

Preparation: Gillespie, MacLaren and Pollock (1970) Br. J. Pharmac. 40, 257.

Pithing rod used as an electrode for electrical stimulation of the cardiac nerves. Blood pressure recorded from left femoral artery, heart rate by tachometer. Shocks of Supramax. voltage, 0.25 Hz; 2 msec width:

—Response of ↑ 138 beats/min sustained tachycardia.

Result
Effect of ARL on tachycardia to preganglionic nerve stimulation

| Drug (μg/kg) | Heart rate (beats/min) | Changes in Mean Blood Pressure (mmHg) |
|---|---|---|
| 0.38 | 0 | ↓ 15 |
| 0.75 | 0 | ↓ 15 |
| 1.5 | 0 | ↓ 15 |
| 3.0 | ↓ 6 | ↓ 20 |
| 6.0 | ↓ 18 | ↓ 15 |
| 12.0 | — | ↓ 15 |

Initial findings indicate pressor responses to noradrenaline or angiotensin II were unaffected.

Conclusion

No major effect on the tachycardia produced by indirect stimulation. Hypotension followed intravenous injections of ARL.

2. Rabbits (1) Intravenous (i.v.) or Intra-arterial (i.a.) injection n=1.

Method

Sex: female; strain: New Zealand White; weight: 2.2 kg.

Anesthesia: Urethane (1.5g/kg) into the ear vein.

Blood pressure measured from femoral artery.

Heart rate recorded using tachometer triggered by arterial pressure waves.

Drug injected into femoral vein or retrogradely into carotid artery.

| | Result | | | | | |
|---|---|---|---|---|---|---|
| Initial blood pressure | 140/72 | (Systolic/diastolic mmHg) | | | | |
| Initial heart rate | 320 | (Beats/min). | | | | |
| | Change in Systolic BP (mmHg) | | Change in Diastolic BP (mmHg) | | Change in Heart rate (Beats/min) | |
| Drug (μg/kg) | i.v. | i.a. | i.v. | i.a. | i.v. | i.a. |
| Vehicle | 0 | 0 | 0 | 0 | 0 | 0 |
| ARL | | | | | | |
| 0.06 | ↓19 | ↓7 | ↓16 | ↓6 | ↓8 | 0 |
| 0.1 | ↓36 | ↓13 | ↓32 | ↓12 | ↓15 | 0 |
| 0.2 | ↓40 | ↓18 | ↓40 | ↓21 | ↓55 | 0 |
| 0.5 | ↓42 | ↓27 | ↓37 | ↓24 | ↓53 | ↓10 |
| 0.9 | ↓43 | ↓29 | ↓38 | ↓28 | ↓55 | ↓40 |

(2) Intra-renal artery. n=2.
Method
Sex: male; weight: 2.5 kg; strain: New Zealand White.
Anesthesia: initially Halothane, then i.v. chloralose (40 mg/kg and pentobarbitone sodium 2 mg/kg).
Blood pressure recorded from left femoral artery.
Heart rate recorded using tachometer triggered from arterial pressure wave.
Central venous pressure (CVP) via jugular vein.
Left renal blood flow using electromagnetic flow-probe.
Drug administered by infusion retrogradely into suprarenal artery.

| | Result | | | |
|---|---|---|---|---|
| Drug (μg/kg/min) | Change in Diastolic BP (mmHg) | Change in Heart rate (beats/min) | Change in Renal blood flow (ml/min) % | Change in CVP (mmHg) |
| Vehicle | 0 | 0 | 0 | 0 |
| ARL | | | | |
| 0.16 | 0 | 0 | ↓25 | 0 |
| 0.4 | 0 | 0 | ↓50 | 0 |
| 0.8 | ↓10 | 0 | ↓70 | 0 |
| 1.6 | ↓10 | 0 | ↓80 | 0 |
| PGE$_2$ 0.4 | 0 | 0 | ↑20 | 0 |
| PGX 0.4 | 0 | 0 | ↑18 | 0 |

(3) Intravenous infusion - after (2) above

| Drug (μg/kg/min) | Change in Systolic BP (mmHg) | Change in Diastolic BP (mmHg) | Change in Heart rate (beats/min) | Change in Renal blood Flow (ml/min) % | Change in CVP (mmHg) |
|---|---|---|---|---|---|
| Vehicle | 0 | 0 | 0 | 0 | 0 |
| ARL | | | | | |
| 0.4 | ↓15 | ↓10 | 0 | ↓20 | 0 |
| 0.8 | ↓15 | ↓10 | 0 | ↓66 | 0 |
| 1.6 | ↓20 | ↓10 | ↑18 | ↓100 | 0 |

Conclusion
Hypotension and bradycardia followed either intravenous or intra-arterial injections of ARL, the effect being greater intravenously. Renal blood flow was reduced after administration by either route.

3. Dog n=1
Method
Sex: female; weight: 15 kg; strain: Labrador.
Anesthesia: chloralose (50 mg/kg) and pentobarbitone sodium (15 mg/kg).
Injections either intravenous or intra-renal arterially (IV or IRA).
Blood pressure recorded from brachial artery.
Central venous pressure (CVP) measured from a catherterized jugular vein.
Renal blood flow (RBF) measured using an electromagnetic flow probe placed around the left renal artery.
Assay tissue —dog blood superfused. Dog portal vein, DPV; rabbit aorta, RA; chick rectum, CR; rat colon, RC.

| Results | |
|---|---|
| 1. ARL (1.25 μg/kg i.v. = 20 μg) caused | (a) slight ↓ BP |
| | (b) slight ↓ CVP |
| | (c) slight ↓ RBF |
| 2. ARL (1 to 20 μg IRA) caused | (a) slight ↓ BP |
| | (b) slight ↓ CVP (delayed) |
| | (c) slight ↓ RBF |
| 3. ARL (0.1 to 1 μg over assay tissues) caused | (a) ↑ tone DPV |
| | (b) ↑ tone RA |
| | (c) no change CR |
| | (d) ↑ tone RC |

Conclusion
Hypotension and reduced renal blood flow after ARL.

4. Guinea Pig —Respiratory studies
(1) Airway resistance and dynamic compliance.
Method
Sex: female, weight: 500 g; strain: Redfern.
Anesthesia: Urethane 7.2 g/kg.
Recorded variables —airways resistance (computed from pressure difference at isovolumetric points divided by flow rate difference at isovolumetric points) Dynamic compliance (Tidal volume/Pleural pressure).
Carotid blood pressure.
Injections made into femoral vein.

| | Result | | | |
|---|---|---|---|---|
| | | | Change in Blood Pressure (mmHg) | |
| Drug (μg/kg) | Change in airway resistance | Change in Compliance | Systolic | Diastolic |
| 1 | ↑50% | ↓40% | ↓30 | ↓11 |

Threshold for hypotension approximately 0.05–0.1 μg/kg.
Threshold for increased airway resistance 1.0–3.0 μg/kg.

(2) Inflation Pressure. n=2
Method
Dixon and Brody (1903). J. Physiol 29, 97.
Pithed guinea pig. Sex: male; weight: 500 g; strain: Redfern
Blood pressure recorded from carotid artery.
Inflation pressure recorded from trachea.

| Drug (μg/kg) | Change in Inflation Pressure | Change in Systolic BP (mmHg) | Change in Diastolic BP (mmHg) | Change in Heart rate (Beats/min) |
|---|---|---|---|---|
| Vehicle | 0 | 0 | 0 | 0 |
| ARL i.v. | | | | |
| 0.1 | 0 | 0 | 0 | 0 |
| 0.3 | ↑3 | ↓3 | ↓3 | 0 |
| 1.0 | ↑70 | ↓22 | ↓12 | — |
| Histamine i.v. | | | | |

-continued

| Drug (μg/kg) | Change in Inflation Pressure | Change in Systolic BP (mmHg) | Change in Diastolic BP (mmHg) | Change in Heart rate (Beats/min) |
|---|---|---|---|---|
| 5.0 | ↑ 50 | ↑ 12 | ↑ 3 | ↑ 12 |

Response to histamine potentiated by ARL.

(3) Superfused isolated tracheal rings

| Results | |
|---|---|
| ARL 10 μg | NO EFFECT (Usual contraction to $PGF_{2\alpha}$). |

Conclusion

Increased airway resistance accompanied by hypotension produced by ARL. Some evidence that a lower dose is required for a threshold hypotensive effect. Constriction of pulmonary vessels could contribute to reduced compliance. Tracheal smooth muscle was unaffected in vitro.

| 5. Superfusion of Isolated Tissues-in vitro | |
|---|---|
| (↑ Contraction; ↓ relaxation). (0 No change) | |
| | Response to ARL (up to 5 μg applied directly over tissue) |
| Rat Colon | ↑ (prolonged, 100–200 ng) |
| Chick Rectum | 0 |
| Rat Stomach Strip | ↑ (prolonged, 100–200 ng) |
| Guinea Pig Ileum | 0 |
| Rabbit Mesenteric artery strip | 0 |
| Rabbit Coeliac artery strip | 0 |
| Rabbit Femoral artery strip | 0 |
| Rabbit Prox vena cava | 0 |
| Rabbit coronary artery | ↓ (100–200 ng) |
| Tissue respond normally to standards, e.g., $PGE_2$ (10 ng) or SRS-A (1–2 units). | |

Conclusion
Contraction of rat color and stomach strip non-vascular smooth muscle. Rabbit coronary artery relaxed but other vessels unaffected.

6. Spontaneously beating atria —in vitro
Method n=3
Guinea pig, weight: 500–615 g; strain: Redfern; sex: female.
Applied tension 1 g.
35° C. Krebs solution.

| Result | |
|---|---|
| Vehicle | - no effect on force or rate of contraction. |
| ARL μg/ml 0.01–4 | - no effect on force or rate of contraction. |

Conclusion
No important effects on force or frequency of atrial contraction.

What is claimed:

1. In the method of producing the ARL compound which includes collecting rabbit medulla, the improvement comprising incubating said rabbit medulla at a temperature and time sufficient to allow the rabbit medulla to produce sufficient material containing the ARL compound to permit ARL to be extracted therefrom in usable and consistent yields.

2. In the method of producing the ARL compound which includes collecting rabbit medulla, the improvement comprising incubating said rabbit medulla at a temperature and time sufficient to allow the medulla to produce sufficient material containing the ARL compound and lipids, extracting the lipids from the material, reducing the material remaining after extracting the lipids, acetylating the material left after extracting the lipids, and purifying the material which has been reduced and acetylated in a silicic acid column and by thin layer chromatography.

* * * * *